US006794384B1

(12) United States Patent
Potter et al.

(10) Patent No.: US 6,794,384 B1
(45) Date of Patent: Sep. 21, 2004

(54) HYDROXYLATION ACTIVATED DRUG RELEASE

(75) Inventors: Gerard Andrew Potter, Leicester (GB); Lawrence Hylton Patterson, Leicester (GB); Michael Danny Burke, Leicester (GB)

(73) Assignee: De Montfort University, Leicester (GB)

( * ) Notice: Subject to any disclaimer, the term of this patent is extended or adjusted under 35 U.S.C. 154(b) by 0 days.

(21) Appl. No.: 09/633,697

(22) Filed: Aug. 7, 2000

Related U.S. Application Data (63) Continuation of application No. PCT/GB99/00416, filed on Feb. 10, 1999.

(30) Foreign Application Priority Data

Feb. 12, 1998 (GB) .............................. 9802957

(51) Int. Cl.[7] .................. C07C 271/14; C07D 239/553; A61K 31/27; A61P 35/00
(52) U.S. Cl. ................... 514/229.8; 514/274; 514/457; 514/481; 514/489; 514/512; 544/102; 544/313; 549/399; 558/271; 560/161
(58) Field of Search ................ 514/229, 274, 514/457, 481, 489, 512; 544/102, 313; 549/399; 558/271; 560/161

(56) References Cited

U.S. PATENT DOCUMENTS

| 5,276,058 A | 1/1994 | Satoh et al. ............... 514/646 |
| 5,287,386 A | 2/1994 | Wade et al. ................ 375/36 |
| 5,430,062 A | 7/1995 | Cushman et al. .......... 514/646 |
| 5,471,170 A | 11/1995 | Genest .................... 330/151 |
| 5,773,435 A | 6/1998 | Kadow et al. ............. 514/214 |
| 5,966,032 A | 10/1999 | Elrabaa et al. ............ 326/84 |
| 6,214,886 B1 | 4/2001 | Potter et al. ............... 514/685 |
| 6,346,550 B2 | 2/2002 | Potter et al. ............... 514/685 |
| 2002/0037296 A1 | 3/2002 | Potter et al. ............... 424/400 |

FOREIGN PATENT DOCUMENTS

| CA | 2109259 | 4/1994 | |
| DE | 4309344 | 9/1949 | |
| DE | 4236237 | 4/1994 | |
| EP | 0 322 738 A2 | 7/1989 | |
| EP | 0642799 | 3/1995 | |
| JP | 56/016474 A2 | * 2/1981 | |
| JP | 56016474 | 2/1981 | ......... C07D/239/54 |
| JP | 61076433 | 4/1986 | |
| JP | 08188546 | 7/1996 | |
| WO | 9712246 | 4/1997 | |
| WO | WO 99/40056 | 8/1999 | |
| WO | WO 99/40944 | 8/1999 | |

OTHER PUBLICATIONS

Draetta, G. and Pagano, M. in "Annual Reports in Medicinal Chemistry, vol. 31", 1996, Academic Press, San Diego, p 241–248.*
Wolff, Manfred E. "Burger's Medicinal Chemistry, 5ed, Part I", John Wiley & Sons, 1995, pp. 975–977.*
Banker, G.S. et al, "Modern Pharmaceutics, 3ed.", Marcel Dekker, New York, 1996, p. 596.*
Shan, Daxian, et al, J. Pharmaceutical Sci., 1997, 86, pp. 765–767.*

(List continued on next page.)

Primary Examiner—Mark L. Berch
Assistant Examiner—Thomas McKenzie
(74) Attorney, Agent, or Firm—Baker Botts, L.L.P (57) ABSTRACT

The present invention concerns prodrugs whose aromatic oxidation, particularly their enzymatic aromatic hydroxylation, results in their activation by the release of a drug moiety. It particularly concerns anti-tumor prodrugs and those which are specifically activated by the hydroxylation activity of the P-450 enzyme CYP1B1. Also provided are methods of detection of aromatic oxidation activity.

13 Claims, 3 Drawing Sheets

OTHER PUBLICATIONS

Amble, Erik; Dale, Johannes, Acta Chem. Scand., Ser. B, B533(8), 584–6 (English) 1979.*

Pamer, Eric G.; So, Magdalene; Davis, Charles E., Mol. Biochem. Parasitol., 33(1), 27–32 (English) 1989.*

Buur, Anders; Bundgaard, Hans, Arch. Pharm. Chemi, Sci. Ed., 12(2), 37–44 (English) 1984.*

Suda, Yasuo; Shimidzu, Kenji; Sumi, Masao; Kusumoto, Shoichi; Nadai, Tanekazu; Yamashita, Shinji, Biol. Pharm. Bull., 16(3), 322–4 (English) 1993.*

Hoang TTV et al., 2001, "Cytochrome P450 CYP1B1 Expression in Human Cervical Intraepithelial Neoplasia" *British Journal of Cancer* 85(Suppl 1):78.

Stanley LA et al., 2001, "Cytochrome P450 Cyp1b1 In Colon Tumorigenesis" *Drug Metabolism Reviews* 33(suppl 1):62.

Suda Y et al., 2001, "Chemical and biological degradation of 5–fluorouracil prodrugs having high serum albumin binding potencies", L3 Answer 1 of 1 *Chem. Abstract* 119:62362.

Buur A et al., 2001, "Prodrugs of 5–fluorouracil, II. Hydrolysis kinetics, bioactivation, solubility and lipophilicity on N–alkoxycarbonyl derivatives of 5–fluorouracil" L2 Answer 1 of 1 *Chem. Abstract* 102:12247.

Tang YM et al., 2000, "Human CYP1B1 Leu432Val gene polymorphism: ethnic distribution in African–Americans, Caucasians and Chinese; oestradiol hydroxylase activity; and distribution in prostate cancer cases and controls" *Pharmacogenetics* 10(9):761–766.

Iyer S et al., 1998, "Induction of Apoptosis in Proliferating Human Endothelial Cells by the Tumor–specific Antiangiogenesis Agent Combretastatin A–4" *Cancer Res.* 58:4510–4514.

Ducki S et al., 1998, "Potent Antimitotic and Cell Growth Inhibitory Properties of Substituted Chalcones" *Bioorg. Med. Chem. Letters* 8(9):1051–1056.

Luch A et al., 1998, "Stable Expression of Human Cytochrome P450 1B1 in V79 Chinese Hamster Cells and Metabolically Catalyzed DNA Adduct Formation of Dibenzo[α,1]pyrene" *Chem. Res. Toxicol.* 11:686–695.

Murray GI et al., 1998, "Enhanced expression of cytochrome P450 in stomach cancer" *Br J Cancer* 77(7):1040–1044.

Ohsumi K et al., 1998, XP–002102895, "Novel Combretastatin Analogues Effective against Murine Solid Tumors: Design and Structure—Activity Relationships" *J. Med. Chem.* 41(16):3022–3032.

Dark GG et al., 1997, "Combretastatin A–4, an Agent That Displays Potent and Selective Toxicity toward Vasculature" *Cancer Res.* 57:1829–1834.

Pettit GR et al., 1995, "Antineoplastic agents 322. Synthesis of combretastatin A–4 prodrugs" *Anti–Cancer Drug Design* 10:299–309.

Tully W et al., 1995, "Preparation of cyclomanganated chalcones and their reactions with methyl acrylate and other α,β–unsaturated carbonyl compounds" *J. Organometallic Chem.* 503(1):75–92.

Klein E, 1994, Chemical Abstracts "Cosmetic compositions containing chalcone derivatives" *Am. Chem. Soc.* 120(1):422 (Abstract 14,657c).

Won CM, 1994, "Kinetics and mechanisms of hydrolysis of tryphostins" *Ind. J. Pharmaceutics* 104:29–40.

Cushman M et al., 1992, XP–000571677, "Synthesis and Evaluation of Analogues of (Z)–1–(4–Methoxyphenyl)–2–(3,4,5–trimethoxyphenyl)ethene as Potential Cytotoxic and Antimitotic Agents" *J. Med. Chem.* 35(12):2293–2306.

Doehmer J et al., 1991, "Chinese Hamster Cells Genetically Engineered for Stable Expression of Cytochromes P450" *Meth. Enzymol.* 206:117–122.

Hussoin S et al., 1991, XP–002102894, "Polyhydroxylated Phenylacrylic Acid Derivatives as New Anti–tumor Agents" *J. Pharmaceut. Sci.* 80(5):416–418.

Barrie et al., 1989, "Inhibition of 17α–Hydroxylase/ C17–C20 Lyase By Bifluranol And Its Analogues" *J. Steroid Biochem.* 33(6):1191–1195.

Pamer EG et al., 1989, "Identification of a developmentally regulated cysteine protease of *Trypanosoma brucei*" *Mol. and Biochem. Parasitology* 33:27–32.

Carmichael J et al., 1987, "Evaluation of a Tetrozolium–based Semiautomated Colorimetric Assay: Assessment of Chemosensitivity Testing" *Cancer Res.* 47:936–942.

Eckert H et al., 1987, "Triphosgene, a Crystalline Phosgene Substitute" *Angew, Chem. Int. Ed. Engl.* 26(9):894–895.

Burke MD et al., 1985, "Ethoxy–, pentoxy– and benzyloxyphenoxazones and homologues: a series of substrates to distinguish between different induced cytochromes P–450" *Biochem Pharmacol* 34(18):3337–3345.

Amble E et al., 1979, "Formation of 2–Oxazolidinones from N–Benzyloxycarbonyl–2,2'–dichlorodiethylamine; Demonstration of Chloride Catalysis" *Acta Chem. Scand.* 33(8):584–586.

1978, "I.26 Fractional Distillation At Atmospheric Pressure" *Vogels Textbook of Practical Organic Chemistry*, 4th Ed. 878:146–155.

McMurray JE et al., 1974, *J. Am. Chem. Soc.* 96(14):4708–9.

Wittig G, et al., 1973, "Methylenecyclohexane" *Org. Synth. Coll.* 5:751–754.

Pappalardo G et al., 1968, XP–002102896, "Relation between structure and antibacterial action of arylthioamides, II. Antibacterial activity, ultraviolet and infrared spectra, and acid hydrolysis of aryl– and arylvinylenethioamides" p. 2014; see abstract & Farmaco, et. Sci. 22(10):808–820 (1967) [*Chemical Abstracts* 68(5):21141r].

Gutsche CD et al., 1959, Chemical Abstracts, "Experiments in the colchicine field" *Am. Chem. Soc.* 53(9):9122–9126.

"Differential Activation of Cyclophosphamide and Ifosphamide by Cytochromes P–450 2B and 3A in Human Liver Microcromes" by Chang et al. (Cancer Research 53; pp. 5629–5637, Dec. 1, 1993.

"Tumor–specific Expression of Cytochrome P450 CYP1B1[1]" by Murray et al. pp. 3026–3031; Cancer Research—Jul. 15, 1997.

"Reductive Metabolism: its Application in Prodrug Activation" by Patterson et al. (XP–002106818) pp. 72–79.

* cited by examiner

HYDROXYLATION ACTIVATED DRUG RELEASE

This is a continuation of copending International application No. PCT/GB99/00416 filed Feb. 10, 1999.

The present invention concerns prodrugs whose aromatic oxidation, particularly their enzymatic aromatic hydroxylation, results in their activation by the release of a drug moiety. It particularly concerns anti-tumour prodrugs and those which are specifically activated by the hydroxylation activity of the P-450 enzyme CYP1B1.

Many conventional cytotoxic drugs are known (for example colchicine, esperimycin, taxol, daunomycin and staurosporin) which can be used for chemotherapeutic purposes. However, they typically suffer from the problem that they are generally cytotoxic and therefore may affect cells other than those which it is wished to target. This can be alleviated somewhat by using targeted drug delivery systems, for example direct injection to a site of tumorous tissue, or by e.g. binding the cytotoxic agent to antibody which specifically recognises an antigen displayed by cancerous cells. Alternatively, electromagnetic radiation may be used to cause chemical changes in an agent at a desired site in the body such that it becomes cytotoxic. However, all of these techniques have, to a greater or lesser extent, certain limitations and disadvantages.

It has been reported (Murray, G. I. et al., Jul. 15, 1997. Cancer Research, 57: 3026–3031) that the enzyme CYP1B1, a member of the cytochrome P450 family of xenobiotic metabolizing enzymes, is expressed at a high frequency in a range of human cancers including cancers of the breast, colon, lung, oesophazus, skin, lymph node, brain and testis, and that it is not detectable in normal tissues. This led to the conclusion (p. 3030, final sentence) that ". . . the expression of CYP1B1 in tumour cells provides a molecular target for the development of new anticancer drugs that could be selectively activated by the presence of CYP1B1 in tumour cells". It was also reported (p.3030, column 1 lines 15–17) that CYP1B1 is capable of 4-hydroxylation of estradiol. No specific anticancer drugs were suggested.

The present inventors have now succeeded in creating a range of prodrugs having a "carrier" framework with a drug moiety conjugated to it (the prodrug other than the drug moiety is referred to below as "the rest of the prodrug") which have little or no cytotoxic effect when in their normal state, but whose aromatic oxidation e.g. hydroxylation (for example by CYP1B1) results in the release of the drug moiety. With CYP1B1 as a hydroxylating enzyme, this provides for a self-targeting drugs delivery system in which a non-cytotoxic (or at least negligibly cytotoxic) compound can be administered to a patient, for example in a systemic manner, the compound then being hydroxylated at the site of tumour cells (intratumoural hydroxylation) to release the drug which acts to kill or otherwise affect the tumour cells. The fact that CYP1B1 is not expressed by normal cells means that the hydroxylation of the prodrug only occurs at the site of tumour cells and therefore only tumour cells are affected, thus providing a self-targeting drug delivery system.

The prodrugs of the present invention have the distinct advantage of being useful in the treatment of tumours at any site in the body, meaning that even tumours which have undergone metastasis (which are not normally susceptible to site-specific therapies) may be treated, as well of course as primary and secondary tumours.

The prodrugs may be designed to be activated by other oxidising agents, for example other enzymes (e.g. other members of the cytochrome P-450 family of enzymes) which cause hydroxylation of the prodrug. For example, a prodrug activated by hydroxylation by the human CYP1A1 isoform would be useful for the treatment of stomach cancer since this isoform is over expressed in this type of cancer (Murray et al., 1998, Br. J. Cancer, 77: 1040). Furthermore, if the prodrug is specifically activated by a fungal P-450 enzyme isoform then it has utility as a selective antifungal agent, and similarly a prodrug specifically activated by a bacterial P-450 enzyme isoform would have utility as a selective antibiotic agent.

CYP1B1 has not yet been fully characterised, and it is therefore possible that tumour-specific isoforms of it may exist which possess the same catalytic properties. The prodrugs of the present invention may, of course, be used with such enzymes.

In the case of cytochrome P-450 activated prodrugs, the therapeutic strategy achieved using them is referred to as SPEAR (Specific P-450 Enzyme Activated drug Release).

According to the present invention there is provided a prodrug comprising a drug moiety bound to a carrier framework, the prodrug being activated by aromatic oxidation of the carrier framework to release the drug moiety.

The prodrug may be activated by aromatic hydroxylation. It may be activated by enzymatic aromatic hydroxylation.

Other enzymatically-activated prodrugs are known, for example those which release a drug moiety as the result of cleavage by a peptidase enzyme. However, nowhere has it been previously suggested that a prodrug could be activated to release a drug moiety by enzymatic hydroxylation.

A prodrug according to the present invention may have the formula (Z):

wherein:
  X=H, OH, OMe or N(CH$_3$)$_2$; and
  n=0–6;
and:
  R$_1$=H, C$_{1-4}$ lower alkyl, or together with R$_2$ forms part of a cycloalkyl group which may be further substituted to form part of a polycyclic cycloalkyl group, or with R$_2$ forms part of a steroidal carbon framework;
  R$_2$=H, OMe, C$_{1-4}$ lower alkyl, or together with R$_1$ and/or R$_3$ forms part of a cycloalkyl, polycyclic cycloalkyl or steroidal carbon framework, or forms part of a polycyclic aromatic group by linkage to R$_4$;
  R$_3$=H, OMe, C$_{1-4}$ lower alkyl or together with R$_2$ forms part of a cycloalkyl, polycyclic cycloalkyl or steroidal carbon framework; and
  R$_4$=H or is fused directly to the aromatic position designated by R$_2$ and either:
    the drug moiety is derived from a drug having a free amino, hydroxyl or thiol group and which links it to the rest of the prodrug, such that A represents NH, NR (R=C$_{1-4}$ lower alkyl), O or S; or the drug moiety is derived from a drug having a carboxylate group, an ester linkage joining it to the rest of the prodrug and A being absent.

Enzymatic hydroxylation of the prodrugs of formula (Z) results in the transfer of electrons from the site of hydroxylation (for example the aromatic 4 position—see FIG. 1) to the drug moiety, resulting in its release.

The prodrug may, for example, be an anti-tumour prodrug. The drug moiety may be cytotoxic or cytostatic, although of course it may be a moiety which has any other desired effect. Examples of classes of drug moiety include antimitotic agents, alkylating agents, antifolates, antimetabolites. DNA-damaging agents and enzyme inhibitors. Specific examples of possible cytotoxic drug moieties include 5-fluorouracil, colchicine, esperimycin, taxol, daunomycin, staurosporin, and nitrogen mustard. Alternatively, the drug moiety could be e.g. a fluorescent organic molecule which would be released in an intratumoural manner, aiding tumour detection by correlating specific cell fluorescence with the presence of the drug moiety and thus of the oxidising agent (e.g. CYP1B1) which caused its release.

Thus the term "drug" also extends to moieties which may be used for diagnostic purposes.

A possible nitrogen mustard is, for example, a para-hydroxy aniline mustard that is linked through the para-hydroxy group to the rest of the prodrug. In the case of nitrogen mustard prodrugs, the mustard function is itself activated only when the drug moiety is released from the prodrug. Another example of a nitrogen mustard which can be incorporated into a SPEAR prodrug is Nor-mustine, which can be linked directly through the mustard nitrogen atom. In this case the carbamate linked nor-mustine prodrug has very low toxicity, but upon enzymatic hydroxylation of the prodrug the potent cytotoxic agent Nor-mustine is released.

The olefin linkage may have a cis- or trans-geometry. It may be acyclic or cyclic. It may form part of an aromatic or polycyclic aromatic system.

The prodrug may be activated by CYP1B1. Thus a prodrug which releases a cytotoxic drug moiety upon hydroxylation by CYP1B1 may be used as a self-targeting anti-tumour drug, being activated at the site of a tumour by CYP1B1 and having no (or negligible) cytotoxicity in the rest of the body.

The linkage to the drug moiety from the carrier framework may be from a hydroxyalkyl group in the prodrug via a carbamate, carbonate or thiocarbonate linker to an amino, hydroxy or thiol group in the drug moiety.

Using the strategy and prodrugs of the present invention, it is possible to link any desired drug moiety through a free amino, hydroxy or thiol group. The provision of a linker group comprising a carbamate, carbonate or thiocarbonate linker joining the drug moiety to the rest of the prodrug results in the release of carbon dioxide upon release of the drug moiety, making the reaction irreversible. Thus the hydroxylation (or other aromatic oxidation) of the prodrug may cause the release of the drug moiety and carbon dioxide.

A prodrug may have a steroid carbon carrier framework. For example, it may be derived from estradiol.

Figure 1:
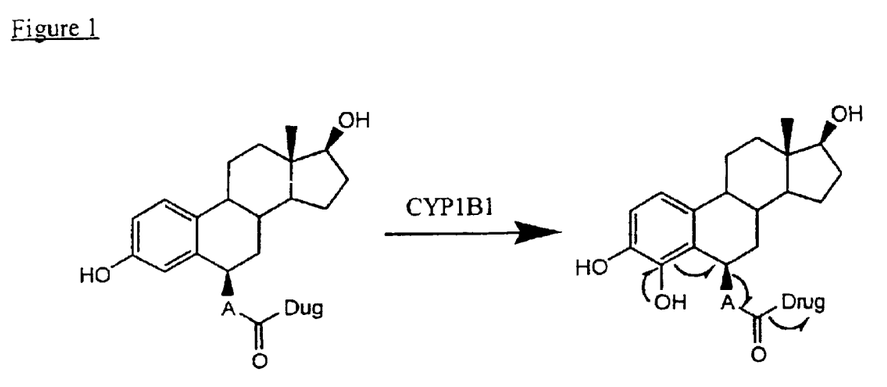
FIG. 1 shows the estradiol-derived prodrug having the formula (I), together with its 4-hydroxylation.

An example of a prodrug according to the present invention is the prodrug having the formula I, shown in FIG. 1. It is an estradiol derivative and incorporates the drug moiety at the steroid 6-position. In this position, the 3-hydroxy group of estradiol does not provide the requisite electron release, but upon 4-hydroxylation the electron release from the 4-hydroxy group triggers electron transfer within the prodrug, resulting in the release of the drug moiety.

A prodrug according to the present invention may, for example, have the formula of any one of formulae (I)–(IX):

(II):

(III):

(IV):

(V):

(VI):

(VII):

(VIII):

(IX):

wherein —OR=—Ome or —OH

The prodrug may have the formula of any one of formulae (X)–(XIII):

(X):

(XI):

(XII):

(XIII):

where R=H (Formula XIIa) or R=Me (Formula IIb)

Figure 3:
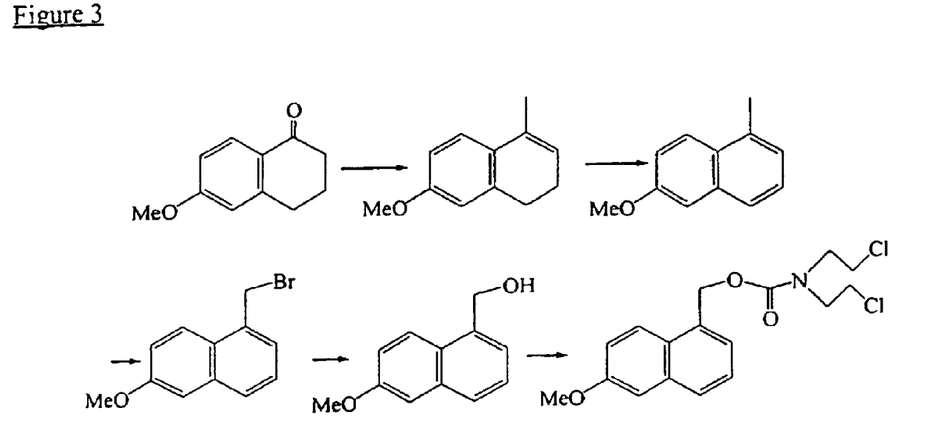
FIG. 3 shows the synthesis of the naphthyl/mustard prodrug starting from 6-methoxy-1-tetralone.

Formula (X) is a colchicine-estradiol prodrug; (XI) is a combretastatin-estradiol prodrug; (XII) is a mustard-estradiol prodrug; (XIII) is a fluorophore-estradiol conjugate. The prodrug may have a polycyclic aromatic carrier framework. For example the prodrug may be based on the naphthyl or phenanthryl structures. Examples of naphthyl based prodrugs and phenanthryl based prodrugs are given by the formulae (XIV) to (XVII) below. The compound (XIV) is a naphthyl/colchicine prodrug, (XV) is a naphthyl/ mustard prodrug, (XVI) is a naphthyl/5-fluorouracil prodrug, and (XVII) is a phenanthryl/mustard prodrug. The synthetic route used for the synthesis of the naphthyl based prodrugs is outlined in the scheme shown in FIG. 3.

(XIV):

(XV):

(XVI):

(XVII):

The prodrug may be based on a substituted benzyl carrier framework. For example the prodrug may be based on various methoxy substituted benzyl groups, and these are exemplified by the benzyl/mustard compounds having formulae (XVIII) to (XXII). Compound (XVIII) is a 3-methoxybenzyl/mustard prodrug, (XIX) is a 3,5-dimethoxybenzyl/mustard prodrug, (XX) is a benzyl/mustard prodrug, (XXI) is a 2-methoxybenzyl/mustard prodrug, and (XXII) is a 2,5-dimethoxybenzyl/mustard prodrug. These compounds have the general formula (Y):

Specific molecules having formulae (XVIII)–(XXII) have groups $R_2$, $R_3$ and X as detailed below:

| Compound | R2 | R3 | X |
|---|---|---|---|
| XVIII | H | H | OMe |
| XIX | H | OMe | OMe |
| XX | H | H | H |
| XXI | OMe | H | H |
| XXII | OMe | H | OMe |

The variety of drugs and fluorophores which may be linked to the benzyl carrier framework is further exemplified by the benzyl based prodrugs given in formulae (XXIII) to (XXVIII). Compound (XXIII) is a 3-methoxybenzyl/5-fluorouracil prodrug, (XXIV) is a 3-methoxybenzyl/colchicine prodrug, (XXV) is a 3-methoxybenzyl/calchone prodrug derived from the cytotoxic calchone (E)-1-(3-Hydroxy-4-methoxyphenyl)-3-(3,4,5-trimethoxyphenyl) prop-1-en-3-one, (XXVI) is a 3-methoxybenzyl/combretastatin prodrug, (XXVII) is a 3-methoxybenzyl/resorufin fluorophore conjugate, and (XXVIII) is a 3-methoxybenzyl/7-amino-4-methylcoumarin fluorophore conjugate.

(XXIII):

(XXIV):

(XXV):

(XXVI):

(XXVII):

(XXVIII):

The prodrug may be based on the cinnamyl carrier framework, and this is exemplified by the cinnamyl based prodrugs given by formulae (XXX) to (XXXII). Compound (XXX) is a 3-methoxycinnamyl/mustard prodrug, (XXXI) is a cinnamyl/resorufin fluorophore conjugate, and (XXXII) is a cinnamyl/7-amino-4-methylcoumarin fluorophore conjugate.

(XXX):

(XXXI):

(XXXII):

Also provided according to the present invention is a prodrug according to the present invention for use in a method of treatment or diagnosis of the human or animal body, particularly the treatment or diagnosis of tumours.

Also provided according to the present invention is the use of a prodrug according to the present invention in the manufacture of a medicament, e.g. for the treatment of tumours.

Also provided according to the present invention is a method of manufacture of a medicament, comprising the use of a prodrug according to the present invention.

Also provided according to the present invention is a method of treatment of a patient, comprising administering to the patient a prodrug according to the present invention. The prodrug may be administered to treat a medical condition e.g. an illness.

Methods of manufacture of medicaments are well known. For example a medicament may additionally comprise a pharmaceutically acceptable carrier diluent or excipient (Remington's Pharmaceutical Sciences and US Pharmacopeia, 1984, Mack Publishing Company, Easton, Pa. USA).

The exact dose (i.e. a pharmaceutically acceptable dose) of prodrug to be administered to a patient may be readily determined by one skilled in the art, for example by the use of simple dose-response experiments.

Since prodrugs of the present invention may be specific to e.g. tumour cells, they may not only be used to treat tumours, but may also be used to determine whether or not a patient (or a sample taken from a patient) has tumour cells. For example, tumour cells may be detected by using a SPEAR prodrug that is a fluorophore conjugate which releases a fluorescent compound upon enzymatic hydroxylation. An example of this type of fluorophore conjugate is given by compound (XIII). Cell numbers in a sample may be assayed, as may the presence and quantity of the oxidised e.g. hydroxylated prodrug, thus providing for the diagnosis of the presence of tumour cells. Another way in which a SPEAR prodrug may be used for diagnosis is by using a carbon-13 isotopically labelled carbonyl linkage. Here the carbon dioxide liberated following aromatic hydroxylation of the prodrug will contain the carbon-13 isotope and can thus be measured by a carbon-13 detection technique such as mass spectrometry. The carbon-13 labelled carbon dioxide would be detectable in the exhaled breath of a patient administered with the prodrug, and therefore this technique provides a means for a diagnostic breath test for cancer. Thus in any diagnostic test, the drug moiety may be anything which, upon aromatic oxidation of the prodrug, results in the release of a detectable product. Thus in a diagnostic test, a detection step may be for any product of aromatic oxidation of the prodrug, for example the drug moiety, carrier framework or other product of aromatic oxidation.

Thus the present invention also provides a method of detection of aromatic oxidation, comprising the steps of:
  i) contacting a sample with a prodrug according to any one of claims 1–26;
  ii) detecting any product of aromatic oxidation of the prodrug; and
  iii) correlating detection of the product of aromatic oxidation of the prodrug with aromatic oxidation activity.

The aromatic oxidation activity may be enzymatic, for example CYP1B1 aromatic oxidation activity.

The method may be a method of detection of tumour cells.

The method may be a method of diagnosis of the human or animal body.

The invention will be further apparent from the following description, with reference to the several figures of the accompanying drawings, which show, by way of example only, forms of prodrug.

Of the figures.

Figure 2:
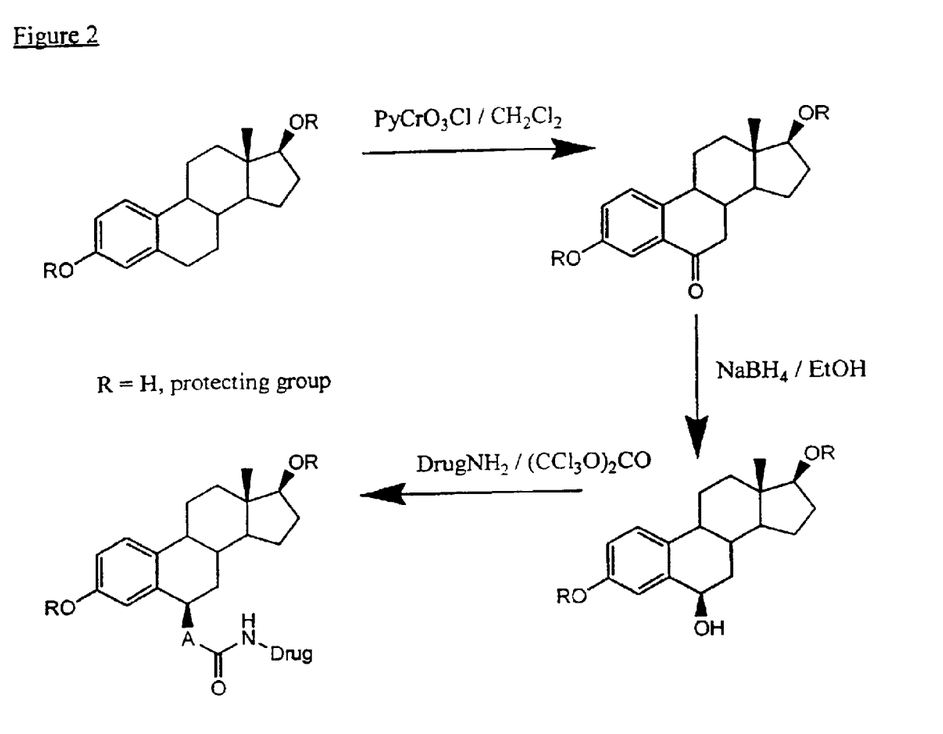
FIG. 2 shows the synthesis of an estradiol-colchicine produg. R is designated as representing H or a protecting group, for example an acetate group ($COCH_3$) or a benzyl group ($CH_2C_6H_5$)

The synthesis of the estradiol-colchicine prodrug I is shown in FIG. 2. The synthetic route uses estradiol as a starting material. The 6-oxo group is introduced by oxidation of estradiol with pyridinium chlorochromate to give 6-oxo estradiol. This is then subjected to borohydride reduction to produce 6-hydroxy estradiol. The desired cytotoxic agent is then coupled to the 6-hydroxy estradiol using triphosgene as coupling agent (Eckert and Foster, 1987, Angew. Chem. Int. Ed. Engl., 26: 894–895) to provide the carbamate linked estradiol prodrug. In the synthesis of the prodrug, the R group is initially a protecting group (for example an acetate group). Once the final step (above) has been taken, the protecting groups are substituted with hydrogen to give the final prodrug product. The chemistry of protecting groups and their substitution is well known and will be readily apparent to one skilled in the art. Where R is a methyl group as exemplified by compound (XIIb) then this group remains in the final product and hence no deprotection step is required in this case.

4-hydroxylation of the prodrug (FIG. 1) results in electron transfer from the 4-hydroxy group, causing release of the drug moiety and carbon dioxide. The release of carbon dioxide makes the reaction irreversible.

The invention is exemplified by the specific SPEAR prodrugs given in the formulae (X) to (XV). Compound (X) is a carbamate linked colchicine-estradiol prodrug, which releases the cytotoxic agent des-acetyl colchicine upon enzymatic hydroxylation by CYP1B1. Compound (XI) is a carbonate linked combretastatin-estradiol prodrug. Compound (XII) is a SPEAR prodrug of a nitrogen mustard, which generates the highly cytotoxic alkylating agent, bis (chloroethyl)amine mustard, upon enzymatic hydroxylation. Compound (XIII) is a SPEAR fluorophore conjugate which releases the fluorescent compound 7-amino-4-methylcoumarin upon enzymatic hydroxylation. Compound (XIV) is an example of a non-steroidal SPEAR prodrug of colchicine linked to 6-methoxy-1-naphthalenemethanol. Compound (XV) is an example of a non-steroidal SPEAR prodrug derived from 3-methoxybenzyl alcohol.

Prodrug Metabolism Studies

A microsomal preparation of resected human tumour tissue expressing the cytochrome P-450 CYP1B1 enzyme was prepared essentially as described by the method of Barrie et al. (1989. J. Steroid Biochem., 6: 1191–1195). The prodrug metabolism experiment was carried out under yellow light, at 37° C.

An array of 1.5 ml centrifuge tubes were set up in a water bath shaker under aerobic conditions. To each tube was added 500 µl of pH 7.6 buffer (0.1 M $NaK_2PO_4$), followed by an aqueous solution of NADPH (5 µl of a 25 mM stock solution). The microsomal preparation (80 µl) was then added and the tubes preincubated for 5 minutes at 37° C. The prodrug substrate was then added (10 µl of a 5 mM stock solution) and incubated for 1 hour at 37° C. After 1 hour the tubes were transferred to an ice/water cooling bath (0° C.). The tubes were then centrifuged at 15,000 rpm for 30 minutes. A sample of the supernatant (100 µl) was then taken and analysed by HPLC, using the following HPLC conditions: Spherisorb C18 (25 cm×4.6 mm id), used without guard column. Flow rate 1 ml/min. Eluent 75% 0.1 M KH2PO4 and 25% acetonitrile. Metabolism of the prodrugs in this way was found to result in release of the free drug moiety. For example, tumour microsomal metabolism of the colchicine-estradiol prodrug compound (X) liberated free N-desacetyl colchicine, which was detected by HPLC analysis.

In vitro Cytotoxicity Studies

The cytotoxicity assay method used was a modification of the MTT cytotoxicity assay (Carmichael et al., 1987, Cancer Research, 47: 936). The activity of the compounds were evaluated in cell lines which express the enzyme CYP1B1 (V79mzhu1B1) and the corresponding parental cell line which does not express CYP1B1 (V79mz) (Luch et al., 1998, Chem. Res. Toxicol., 11: 686). 103 cells were plated in 100 ml DMEM (high glucose) (Dulbecco's Modified Eagles Medium, Life Science International.) plus 10% heat-inactivated FBS (Foetal Bovine Serum, Hybrimax, Sigma.) per well of 96 well (Nunc) microtitre plates for 24 hours to allow adherence and metabolic recovery followed by addition in quadruplicate of compound at double strength in the same medium in 100 ml to give a final maximal concentration of 0.2% DMSO. Compound stocks were made up as 100 mM in DMSO and stored for no more than one month at 4° C. The plates were then incubated at 37° C., 5% $CO_2$, 100% humidity for a further 48 hours followed by washing by immersion 3 times in Dulbecco's PBS A. 50 ml of RPMI 1640 w/o phenol red (Roswell Park Memorial Institute Medium 1640, Life Science International.) with 2 mg/ml MTT was then added for four hours as above, excess MTT removed by aspiration and 125 ml of DMSO added on a vortex for 30 minutes to solubilize the product. The absorbance at A450 was recorded and the results expressed as a % survival of carrier only treated controls. From this data was calculated the IC50 value, which is the concentration at which 50% cytotoxicity is observed. Confirmation of expression of CYP1B1 was determined by immunocytology. Western blotting and EROD (ethoxyresorufin-O-dealkylase assay; Burke, M. D. et al., 1985, Biochem. Pharmacol., 34: 3337) assay of cells used in the assay at the time point when the compounds were added, either fixed in methanol at −20° C., or harvested from replicate plates and stored at −80° C. until assay.

The prodrugs were evaluated using the above assay system, and the results are shown in Table 1. These results demonstrate that the compounds of this invention exhibit differential toxicity against the CYP1B1 expressing cell line.

From Table 1 it is seen that compound XVIII (DMU-313) and compound XIX (DMU-315) are 3-fold more cytotoxic against the cell line expressing CYP1B1 demonstrating that the compounds of this invention are useful as tumour selective anticancer agents against tumours expressing the CYP1B1 enzyme.

Prodrug Synthesis

Section 1: Estradiol Based Prodrugs

Estradiol 3,17-Dipiyaloate

Pivaloyl chloride (664 mg; 5.5 mmol) was added dropwise to a solution of estradiol (250 mg; 0.9 mmol) in 1:1 pyridine/dichloromethane (3 ml) at 0° C. After 15 h the reaction was quenched with water (10 ml) and the product was extracted with ether (3×10 ml). The combined organic layers were washed sequentially with 10% HCl (15 ml), saturated aqueous copper sulfate (15 ml) and brine (15 ml), dried over MgSO4 and finally concentrated in vacuo. The residue was recrystallised from hot ethanol and isolated as a white crystalline solid (247 mg; 61%). IR (cm−1, KBr): (3000, CH) (1700, COO)(1500, ArC═C) (1300, CH3); 1H-NMR (250 MHz, CDCl3): (H (0.9, s; 3H) (1.2, s; 9H) (1.3, s; 9H) (1.4, m; 6H) (1.8, m; 3H) (2.3, m; 3H) (2.9, t; 2H) (4.7, t; 1H) (6.8, m; 2H) (7.1, d; 1H): 13C-NMR (250 MHz, CDCl3): (c 12.0, 23.3, 26.1, 27.0, 27.1, 27.2, 27.6, 29.5, 36.9, 38.2, 38.8, 39.9, 43.1, 43.9, 49.8, 82.2, 118.4, 121.3, 126.3, 137.5, 138.0, 148.9, 157.8, 177.3, 178.5; Mass Spectrum (M+1) m/e=441.

6-Oxoestradiol 3,17-Dipivaloate (DMU-309)

3,5-Dimethylpyrazole (545 mg; 5.7 mmol) was added to a suspension of chromium trioxide (576 mg; 5.7 mmol) at −20° C. in dichloromethane (2 ml). After stirring for 15 min, estradiol 3,17-dipivaloate (250 mg; 0.57 mmol) in dichloromethane (1 ml) was added dropwise and the reaction mixture was stirred at −15° C. for 4 h. The reaction was quenched with water (15 ml) and the aqueous layer was extracted with ether (3×15 ml). The combined organic layers were washed with water (15 ml) and brine (15 ml), dried over MgSO4 and concentrated in vacuo. The residue was chromatographed on silica gel and the product was isolated as a white solid (55 mg; 21%). IR (cm−1, KBr): (3000, CH) (1700, COO) (1650, ArCO) (1500, ArC=C) (1300, CH3); 1H NMR (CDCl3): (H(0.9, s; 3H) (1.2, s; 9H) (1.39, d; 9H) (1.41, m; ,6H) (1.9, m; 2H) (2.2, m; 2H) (2.3, m; 1H) (2.4, m 1H) (2.7, d; 1H) (4.7, t; 1H) (7.2, d; 1H) (7.4, d; 1H)(7.6, d; 1H); 13C NMR (CDCl3): (c 11.9, 22.9, 25.3, 27.1, 27.2, 27.4, 36.5, 38.9, 39.1, 39.5, 42.9, 43.0, 43.8, 49.8, 81.7, 119.9, 126.6, 126.9, 133.6, 144.0, 149.8, 178.4, 196.9; Mass Spectrum (M+1) m/e=455.

6-Hydroxyestradiol 3,17-Dipivaloate (DMU-310)

Sodium borohydride (104 mg; 2.8 mmol) was added to 6-oxoestradiol-3,17-dipivaloate (500 mg; 1.1 mmol) in ethanol (20 ml) at 25° C. under nitrogen. The reaction was quenched with water (100 ml) after 48 h, and the aqueous layer was extracted with diethyl ether (3×50 ml). The organic layers were combined, dried over MgSO4 and concentrated in vacuo. The product was purified on silica gel and isolated as an off-white solid (150 mg; 30%). IR (cm$^{-1}$; KBr): (3500; OH) (2900: CH); $^1$H-NMR CDCl$_3$: (0.8, s; 3H) (1.1, s; 9H) (1.3, m: 10H) (1.4, m; 9H) (2.2, m; 3H) (4.7, t; 1H) (4.8, t; 1H) (6.9, dd; 1H) (7.2, m; 1H); $^{13}$C-NMR CDCl$_3$; 12.1, 23.3, 27.3, 36.9, 37.8, 43.1, 44.5, 49.3, 69.8, 82.1, 120.0, 120.5, 126.4, 137.3, 140.9: Mass Spectrum (M+1l) m/e=457.

Compound (X): Estradiol-Colchicine Prodrug (DMU-327)

To a solution of triphosgene (0.25 mmol, 74 mg) in dichloromethane (1 ml) was added a solution of 6-hydroxyestradiol 3,17-dipivaloate (0.3 mmol, 137 mg) and diisopropyethylamine (0.6 mmol, 0.1 ml) in dichloromethane (1.5 ml). The mixture was stirred for 30 min, then a solution of N-desacetyl colchicine (0.3 mmol, 107 mg) and diisopropylethylamine (0.6 mmol, 0.1 ml) in dichloromethane (1.5 ml) was added and the mixture stirred for 1 h. The reaction mixture was then evaporated to dryness, the residue redissolved in ethylacetate, and washed with 0.5 M NaCO3 (aq). The ethylacetate solution was then dried over MgSO4, and concentrated in vacuo to furnish the title prodrug as its 3,17-dipivaloate ester. The prodrug dipivaloate ester was then dissolved in methanol (3 ml) and an aqueous solution of methylamine (40% w/w. 0.5 ml) added, and the solution stirred for 1 h. Dilute HCl (0.1 M) was then added to neutralise the mixture to pH 7, and the product then extracted with dichloromethane (3×10 ml). The solvent was then evaporated in vacuo to give the title estradiol-colchicine prodrug. IR (KBr) 1695 cm−1; MS (M+1) m/e= 672.

Compound (XI): Estradiol-Combretastatin Prodrug (DMU-328)

The procedure followed that described for compound (X) above, but using combretastatin (0.3 mmol, 95 mg) in place of N-desacetyl colchicine, to afford the title estradiol-combretastatin prodrug. IR (KBr) 1750 cm−1: MS (M+1) m/e=631.

Compound (XIIa): Estradiol-Mustard Prodrug (DMU-329)

The procedure followed that described for compound (X), but using bis(chloroethyl)amine hydrochloride (0.3 mmol, 53 mg) in place of N-desacetyl colchicine together with an extra equivalent of diisopropylethylamine (0.6 mmol, 0.1 ml). This gave the title estradiol-mustard prodrug as a white crystalline compound. IR (KBr) 1700 cm−1; MS (M+1) m/e=456.

Compound (XIII): Estradiol-Fluorophore Conjugate (DMU-330)

The procedure followed that described for compound (X), but using 7-amino4-methylcoumarin (0.3 mmol, 53 mg) in place of N-desacetyl colchicine, to afford the title estradiol-fluorophore conjugate. IR (KBr) 1690 cm−1; MS (M+1) m/e=490.

Estradiol 3,17-Dimethyl Ether

Sodium hydride (1.76 g; 44 mmol) was added portionwise to a solution of estradiol (1 g; 3.6 mmol) in anhydrous THF (15 ml) at room temperature. After stirring for five minutes methyl iodide (2.7 ml; 44 mmol) was added dropwise and the reaction was left to stir for 3 h. The reaction was quenched with water (15 ml) and the aqueous layer was extracted with ether (3×15 ml). The combined organic phase was dried over magnesium sulfate and concentrated in vacuo to give a white solid. The crude product was triturated with hexane and recrystallised from hot ethanol to give the title compound as a white crystalline solid (670 mg; 60%). IR cm$^{-1}$ (KBr) 2900 (CH), 1500 (ArC=C), 1250 (OMe); $^1$H-NMR (CDCl$_3$) 0.8 (s, 3H), 1.1 (m, 9H), 1.8 (m, 4H), 2.85 (m, 3H), 3.3 (t, 1H) 3.4 (s, 3H), 3.8 (s, 3H), 6.6 (d, 1H), 6.7 (dd, 1H), 7.2 (d, 1H); $^{13}$C-NMR (CDCl$_3$) 11.6, 23.1, 26.5, 27.3, 27.8, 29.8, 38.1, 38.6. 43.3, 43.9, 50.3, 55.3, 57.9, 90.8, 111.5, 113.8, 126.4, 132.7, 138.0, 157.4; Mass Spectrum (M+1) m/e=301.

6-Oxoestradiol 3,17-Dimethyl Ether (DMU-303)

3,5-Dimethylpyrazole (3.2 g; 32 mmol) was added to a suspension of chromium trioxide (3.33 g; 32 mmol) at −20° C. in anhydrous dichloromethane (15 ml). After stirring for 15 min, estradiol 3,17-dimethyl ether (500 mg; 1.6 mmol) in anhydrous dichloromethane (5 ml) was added dropwise and the reaction mixture was stirred at −15° C. for 4h. The reaction was quenched with water (20 ml) and the aqueous layer was extracted with ether (3×20 ml). The combined aqueous layers were washed with water (3×20 ml), brine (3×20 ml), dried over magnesium sulfate and concentrated in vacuo. The residue was chromatographed on silica gel and the product was isolated as a white solid (60 mg; 11.4%). IR (cm$^{-1}$; KBr): (3000; CH) (1680; CO) (1250; OCH$_3$); $^1$H-NMR CDCl$_3$; (0.8, s; 3H) (1.2, m; 12H) (2.7, dd; 1H) (3.3, t; 1H) (3.4, s; 3H) (3.9, s; 3H) (7.1, d; 1H) (6.7, dd; 1H) (7.3, d; 1H) (7.6, d; 1H); $^{13}$C-NMR CDCl$_3$: 11.4, 19.5, 22.8, 25.6, 37.5, 39.9, 42.9, 44.1, 50.2, 55.5, 57.9, 90.4, 109.7, 121.5, 126.6, 133.4, 139.7, 150.0, 158.21, 180.34, 198.2; Mass Spectrum (M+1) m/e: 315.

6-Hydroxyestradiol 3,17-Dimethy Ether (DMU-304)

Sodium borohydride (3.3 mg; 0.085 mmol) was added to 6-oxoestradiol 3,17-dimethyl ether (55 mg; 17 mmol) in ethanol (1.5 ml) at room temperature under nitrogen. The reaction was quenched with water (5 ml) after 62h, and the aqueous layer was extracted with ether (3×5 ml). The organic layers were combined, dried over magnesium sulfate, and concentrated in vacuo. The product was purified on silica gel and isolated as a white solid (22 mg; 39%). IR (cm$^{-1}$; KBr): (3450; OH) (2900; CH) (1500; ArCH); $^1$H-NMR CDCl$_3$: (0.8, s; 3H) (1.1, m; 9H) (1.8, m; 4H) (2.85, m; 3H) (3.3, t; 1H) (3.4, s; 3H) (3.8, s; 3H) (6.6, d; 1H) (6.7, dd; 1H)(7.2, d; 1H); $^{13}$C-NMR CDCl$_3$: 11.5, 25.0, 26.4, 27.7, 37.9, 38.2, 43.4, 44.0, 49.7, 55.3, 57.9, 70.1, 90.7, 111.8, 113.8, 126.4, 132.4, 140.8, 158.1; Mass Spectrum (M$^+$) m/e: 316

Compound (XIIb): Estradiol Dimethyl Ether/ Mustard Prodrug (DMU-333)

To a solution of triphosgene (0.25 mmol, 74 mg) in dichloromethane (1 ml) was added a solution of 6-hydroxyestradiol 3,17-dimethy ether (0.3 mmol, 95 mg) and diisopropylamine (0.6 mmol, 0.1 ml) in dichloromethane (1.5 ml). The mixture was stirred for 30 min, then a solution of bis(chloroethyl)amine hydrochloride (0.3 mmol, 53 mg) and diisopropylamine (1.2 mmol, 0.2 ml) in dichloromethane (1.5 ml) was added and the mixture stirred for 1 h. The reaction mixture was then evaporated to dryness, the residue redissolved in ethylacetate, and washed with 0.5 M NaCO3 (aq). The ethylacetate solution was then dried over MgSO4, and concentrated in vacuo to furnish the title estradiol dimethyl ether/mustard prodrug. IR (KBr) 1700 cm–1; MS (M+1) m/e=484.

Section 2: Naphthyl Based Prodrugs

6-Methoxy-1-methyl-1,2-dihydronaphthalene

Methyllithium (1M solution in THF; 27 ml, 27 mmol) was added slowly to a solution of 6-methoxy-1-tetralone (3.16 g, 18 mmol) in THF (15 ml) under N$_2$. The reaction mixture was allowed to react under N$_2$ at RT overnight (12 h). It was then diluted with ethyl acetate and quenched with ice-cooled HCl (2M). The aqeous phase was extracted further with ethyl acetate, dried, and concentrated in vacuo. Chromatographic purification of the crude material on silica gel, using 5% ether in petroleum ether as eluent, gave the title compound as a gum (1.6 g, 52%). 1H-NMR (250 MHz CDCl$_3$): 2.1 (t, 3H, Me), 2.2 (m, 2H), 2.8 (t, 2H), 3.8 (s, 3H, OMe), 5.8 (t, 1H), 6.8–7.2 (m, 3H), 13C-NMR (250 MHz, CDCl$_3$) 19.3, 23.2, 28.9, 55.2, 110.8, 113.7, 122.9, 123.9, 129.1, 131.8, 138.1, 158.4; Mass Spectrum (M+1) m/e=175.

6-Methoxy-1-methylnaphthalene

Tetrachloro-1,2-benzoquinone (3.6 g, 14.5 mmol) was added in one portion to a stirred solution of 6-methoxy-1-methyl-1,2-dihydronaphthalene (2.3 g, 13.2 mmol) in diethyl ether (20 ml). The reaction was concetrated down after 24h and purified by column chromatography using petroleum ether as eluent to gave the title compound as a white solid (1.2 g, 53%). 1H-NMR (250 MHz, CDCl$_3$) 2.5 (s, 3H), 3.8 (s, 3H), 7.0–7.8 (m, 6H), 13C-NMR (250 MHz, CDCl$_3$) 19.3, 55.2, 106.5, 118.1, 124.4, 125.2, 125.7, 126.2, 128.0, 134.2. 134.7, 157.3; Mass Spectrum (M+1) m/e=173.

6-Methoxy-1-naphthalenemethyl Bromide

To a solution of 6-methoxy-1-methylnaphthalene (100 mg, 0.58 mmol) in carbon tetrachloride (8 ml) was added N-bromosuccinimide (110 mg, 0.64 mmol), followed by benzoyl peroxide (10 mg). The reaction mixture was refluxed for 5h, then allowed to cool to ambient temperature. The mixture was then filtered to remove the white solid that had formed, and the filtrate concentrated. Chromatographic purification on silica gel, using 2% ethyl acetate in petroleum ether as eluent, gave the title compound as a white solid (115 mg, 79%). 1 H-NMR (CDCl$_3$) 4.0 (s, 3H, OMe), 4.9 (s, 2H, CH$_2$Br), 7.1–8.1 (m, 6H); 13C-NMR (CDCl$_3$) 31.8, 55.2, 106.9, 119.2, 125.3, 125.6, 126.0, 126.5, 133.3, 135.4, 157.8; Mass Spectrum (M+1) m/e=251.

6-Methoxy-1-naphthalenemethanol (DMU-321)

Finely ground NaOH (44 mg, 1.1 mmol) was added to a stirred solution of 6-methoxy-1-naphthalenemethyl bromide (251 mg, 1 mmol) in DMF (5 ml, containing 1% H$_2$O). The reaction was left overnight (10 h), and was then diluted with ethyl acetate, followed by a water wash. The organic phase was dried over Mg$_2$SO$_4$ and concetrated in vacuo. Purification by column chromatography, using CH$_2$Cl$_2$ as eluent, gave the title compound as a white solid (76 mg, 41%). 1H-NMR (CDCl$_3$) 3.8 (s, 3H, OMe), 4.9 (s, 2H, CHOH), 7.0–7.8 (m, 6H); 13C-NMR (CDCl$_3$) 55.3, 63.7 (C—OH), 106.7, 118.9, 123.2, 125.5, 126.0, 126.7, 127.5, 135.2. 136.4, 157.5); Mass Spectrum (M+1) m/e=189.

Compound (XIV): Naphthyl-Colchicine Prodrug (DMU-331)

To a solution of triphosgene (0.25 mmol, 74 mg) in dichloromethane (1 ml) was added a solution of 6-methoxy-1-naphthalenemethanol (0.3 mmol, 56 mg) and diisopropylamine (0.6 mmol, 0.1 ml) in dichloromethane (1.5 ml). The mixture was stirred for 30 min, then a solution of N-desacetyl colchicine (0.3 mmol, 107 mg) and diisopropylamine (0.6 mmol, 0.1 ml) in dichloromethane (1.5 ml) was added, and the mixture stirred for an additional 1 h. The reaction mixture was then evaporated to dryness, the residue redissolved in ethylacetate, and washed with 0.5 M NaCO3 (aq). The ethylacetate solution was then dried over MgSO4, and concentrated in vacuo to furnish the title naphthyl-colchicine prodrug. IR (KBr) 1695 cm–1; MS (M+1) m/e= 572.

Compound (XV): Naphthyl-Mustard Prodrug (DMU-322)

A solution of 6-methoxy-1-naphthalenemethanol (67 mg, 0.36 mmol) and diisopropyl ethylamine (102 mg, 138 µl, 0.79 mmol) in CH$_2$Cl$_2$ (1 ml) was added slowly to a stirred solution of triphosgene (107 mg, 0.36 mmol) in CH$_2$Cl$_2$ (0.5 ml) under a nitrogen atmosphere. After 10 min a solution of bis(2-chloroethyl)amine hydrochloride (63 mg, 0.36 mmol) in CH$_2$Cl$_2$ (1 ml) was added to the above reaction mixture. The reaction was allowed to proceed for 4 h, then quenched with dilute aqueous HCl (1 M). The reaction mixture was then extracted with ethyl acetate and the organic phase was dried over Mg$_2$SO$_4$ and concetrated in vacuo to give the crude product. Chromatography using CH$_2$Cl$_2$ as eluent afforded the title naphthyl-mustard prodrug (80 mg, 63%). IR (KBr) 1701 cm–1; 1H-NMR (CDCl$_3$) 3.4 (t, 2H, CH$_2$N), 3.6 (t, 2H, CH$_2$N), 3.7 (bs, 4H), 3.9 (s, 3H), 5.6 (s, 2H), 7.2–7.9 (m, 6H); 13C-NMR (CDCl3) 41.9, 50.7, 51.3, 55.3, 66.2, 106.8, 119.2, 125.1, 125.3, 125.9, 127.1, 128.3, 131.6, 135.2, 157.6, 189.5; Mass Spectrum (M+1) m/e=356.

Compound (XVI): Naphthyl/5-Fluorouracil Prodrug (DMU-339)

To a solution of triphosgene (0.25 mmol, 74 mg) in dichloromethane (1 ml) was added a solution of 6-methoxy-1-naphthalenemethanol (0.3 mmol, 56 mg) and diisopropylamine (0.6 mmol, 0.1 ml) in dichloromethane (1.5 ml). The mixture was stirred for 30 min, then a suspension of 5-fluorouracil (0.3 mmol, 40 mg) in a solution containing diisopropylamine (0.6 mmol, 0.1 ml) in dichloromethane/dimethylformamide (1:1; 1.5 ml) was added, and the mixture stirred for an additional 1 h. The reaction mixture was then evaporated to dryness, the residue redissolved in ethylacetate, and washed with 0.5 M NaCO3 (aq). The ethylacetate solution was then dried over MgSO4, and concentrated in vacuo to furnish the title naphthyl/5-fluorouracil prodrug. IR (KBr) 1695 cm–1; MS (M+1) m/e=345.

Section 3: Phenanthryl Based Prodrugs

Compound (XVII): Phenanthryl-Mustard Prodrug (DMU-334)

A solution of 7-methoxy-1-phenanthrenemethanol (119 mg, 0.50 mmol) and diisopropyl ethylamine (194 mg, 260 $\mu$l, 1.50 mmol) in $CH_2Cl_2$ (1.5 ml) was added slowly to a stirred solution of triphosgene (148 mg, 0.50 mmol) in $CH_2Cl_2$ (0.5 ml) under a nitrogen atmosphere. After 10 min a solution of bis(2-chloroethyl)amine hydrochloride (89 mg, 0.50 mmol) in $CH_2Cl_2$ (1.5 ml) was added to the above reaction mixture. The reaction was allowed to proceed for 4h, then quenched with dilute aqueous HCl (1 M). The reaction mixture was then extracted with ethyl acetate, and the organic phase was dried over $Mg_2SO_4$ and concetrated in vacuo to give the crude product. Chromatography using $CH_2Cl_2$ as eluent afforded the title phenanthryl-mustard prodrug (240 mg, 59%). IR (KBr) 1700 cm–1; Mass Spectrum (M+1) m/e=406.

Section 4: Benzyl Based Prodrugs

Compound (XVIII): 3-Methoxybenzyl/Mustard Prodrug (DMU-313)

To a solution of triphosgene (166 mg; 56 mmol) in dichloromethane (1 ml) was added dropwise a solution of 3-methoxybenzyl alcohol (77 mg; 56 mmol) and diisopropylethylamine (0.214 ml; 1.23 mmol) in anhydrous dichloromethane (1 ml). After 20 min of stirring at room temperature a solution of bis(2-chloroethyl)amine hydrochloride (100 mg; 56 mmol) and diisopropylethylamine (0.312 ml; 1.79 mmol) in anhydrous dichloromethane (1 ml) was added dropwise and the mixture was stirred for 18h. The reaction was quenched with water (10 ml) and the aqueous layer was extracted with ether (3×10 ml). The combined organic layers were washed with 2M aqueous hydrochloric acid (3×10 ml), brine (3×10 ml), dried over magnesium sulfate, and concentrated in vacuo. The residue was chromatographed on silica gel and the product was isolated as an oil (60 mg; 35%). IR (cm⁻; KBr): (1700; CO) (1500; ArC=C) (1250; $OCH_3$); $^1$H-NMR $CDCl_3$: (3.6, s; 8H) (3.8, s; 3H) (5.1, s; 2H) (6.9, q; 3H) (7.3, t; 3H); $^{13}$C-NMR $CDCl_3$: 41.9, 50.7, 51.3, 55.3, 67.5, 113.3, 113.8. 120.1, 129.7, 137.7, 155.8, 159.8; Mass Spectrum (M⁺) m/e: 305.

Compound (XIX): 3,5-Dimethoxybenzyl/Mustard Prodrug (DMU-315)

The procedure followed that described for compound (XVIII), but using 3,5-dimethoxybenzyl alcohol (500 mg, 2.97 mmol) in place of 3-methoxybenzyl alcohol. This gave the title 3,5-dimethoxybenzyl/mustard prodrug as a waxy solid (382 mg: 38%). IR (cm–1; KBr): (1700; CO) (1500; ArC=C); $^1$H-NMR $CDCl_3$: (3.7, s; 8H) (3.8, s; 6H) (5.1, s; 2H) (6.4, t; 1H)(6.5, d; 2H); $^{13}$C-NMR $CDCl_3$: 41.9, 50.7, 51.2, 55.3, 67.4, 100.2, 105.5, 138.4, 155.6, 160.9. Mass Spectrum (M⁻) m/e: 335.

Compound (XX): Benzyl/Mustard Prodrug (DMU-311)

The procedure followed that described for compound (XVIII), but using benzyl alcohol (500 mg, 4.62 mmol) in place of 3-methoxybenzyl alcohol. This gave the title benzyl/mustard prodrug as an oil (247 mg; 39%). IR (cm⁻¹; KBr): (1700; CO) (1500; ArC=C). $^1$H-NMR $CDCl_3$: (3.6, m; 8H) (3.8, s; 3H) (5.1, s; 2H) (7.4, s; 5H); $^{13}$C-NMR $CDCl_3$: 41.9, 50.6, 51.1, 67.6, 127.9, 127.9, 128.2 128.4, 128.6, 136.2, 155.6. Mass Spectrum (M⁻) m/e: 275.

Compound (XXI): 2-Methoxybenzyl/Mustard Prodrug (DMU-312)

The procedure followed that described for compound (XVIII), but using 2-methoxybenzyl alcohol (500 mg; 3.62 mmol) in place of 3-methoxybenzyl alcohol. This gave the title 2-methoxybenzyl/mustard prodrug as a waxy solid (166 mg; 15%). IR (cm⁻¹; KBr): (1700; CO) (1500; ArC=C). $^1$H-NMR $CDCl_3$: (3.6, d; 8H) (3.8, s; 3H) (5.2, s; 2H) (6.9, m; 2H); $^{13}$C-NMR $CDCl_3$: 42.0, 50.8, 51.8, 55.4, 61.8, 63.5, 110.5, 120.4, 124.4, 129.6, 129.7, 155.9, 157.6; Mass Spectrum (M⁺) m/e: 305.

Compound (XXII): 2,5-Dimethoxybenzyl/Mustard Prodrug (DMU-338)

The procedure followed that described for compound (XVIII), but using 2,5-dimethoxybenzyl alcohol (500 mg; 2.97 mmol) in place of 3-methoxybenzyl alcohol. This gave the title 2,5-dimethoxybenzyl/mustard prodrug as an oil (354 mg; 35%). IR (cm⁻¹; KBr): (1700; CO) (1500; ArC=C); $^1$H-NMR $CDCl_3$: (3.5, m; 8H) (3.8, d; 6H) (5.1, s; 2H) (6.8, m; 21H) (7.0, t; 1H); $^{13}$C-NMR $CDCl_3$: 34.2, 42.8, 43.3, 47.9, 53.1, 55.1, 104.9, 113.4, 116.3, 122.1, 139.6, 144.9, 147.9, 157.9; Mass Spectrum (M⁺) m/e: 335.

Compound (XXIII): 3-Methoxybenzyl/5-Fluorouracil Prodrug (DMU-335)

To a solution of triphosgene (1.6 mmol, 474 mg) in dichloromethane (5 ml) was added a solution of 3-methoxybenzyl alcohol (1.92 mmol, 265 mg) and diisopropylethylamine (3.8 mmol, 0.6 ml) in dichloromethane (10 ml). The mixture was stirred for 30 min, then a suspension of 5-fluorouracil (1.92 mmol, 250 mg) in a solution containing diisopropylethylamine (3.8 mmol, 0.6 ml) in dichloromethane/dimethylformamide (1:1; 3 ml) was added, and the mixture stirred for 1 h. The reaction mixture was then evaporated to dryness, the residue redissolved in ethylacetate, and washed with 0.5 M NaCO3 (aq). The ethylacetate solution was then dried over MgSO4, and concentrated in vacuo to furnish the title 3-methoxybenzyl/5-fluorouracil prodrug. IR (KBr) 1695 cm–1; $^1$H-NMR ($CD_3OD$) 3.8 (s, 3H), 5.4 (s, 2H), 6.9 (dd, 1H), 7.0 (t, 2H), 7.3 (t, 1H), 8.2 (d, 1H); MS (M+1) m/e=295.

Compound (XXIV): 3-Methoxybenzyl/Colchicine Prodrug (DMU-332)

To a solution of triphosgene (0.25 mmol, 74 mg) in dichloromethane (1 ml) was added a solution of 3-methoxybenzyl alcohol (0.3 mmol, 41 mg) and diisopropylethylamine (0.6 mmol, 0.1 ml) in dichloromethane (1.5 ml). The mixture was stirred for 30 min, then a solution of N-desacetyl colchicine (0.3 mmol, 107 mg) and diisopropylethylamine (0.6 mmol, 0.1 ml) in dichloromethane (1.5 ml) was added and the mixture stirred for 1 h. The reaction mixture was then evaporated to dryness, the residue redissolved in ethylacetate, and washed with 0.5 M NaCO3 (aq). The ethylacetate solution was then dried over MgSO4, and concentrated in vacuo to furnish the title 3-methoxybenzyl/colchicine prodrug. IR (KBr) 1695 cm−1; MS (M+1) m/e= 522.

Compound (XXV): 3-Methoxybenzyl/Calchone Prodrug (DMU-337)

To a solution of triphosgene (0.25 mmol, 74 mg) in dichloromethane (1 ml) was added a solution of 3-methoxybenzyl alcohol (0.3 mmol, 41 mg) and diisopropylethylamine (0.6 mmol, 0.1 ml) in dichloromethane (1.5 ml). The mixture was stirred for 30 min, then a solution of the calchone (E)-1-(3-Hydroxy-4-methoxyphenyl)-3-(3,4,5-trimethoxyphenyl)prop-1-en-3-one (100 mg, 0.29 mmol) and diisopropylethylamine (0.6 mmol, 0.1 ml) in dichloromethane (1.5 ml) was added, and the mixture stirred for 1 h. The reaction mixture was then evaporated to dryness, the residue redissolved in ethylacetate and washed with 0.5 M NaCO3 (aq). The ethylacetate solution was then dried over MgSO4, and concentrated in vacuo to furnish the title 3-methoxybenzyl/calchone prodrug. IR (KBr) 1750 cm−1; 1H-NMR (CDCl$_3$) 3.8 (s, 3H), 3.9 (s, 3H), 4.0 (d, 9H), 5.3 (s, 2H), 6.9 (m, 6H), 7.2 (m, 6H), 7.8 (d, 2H); 13C-NMR (CDCl3) 55.3, 56.1, 56.5, 61.0, 70.5, 105.9, 112.6, 113.8, 114.3, 120.5, 121.3, 128.0, 128.9, 129.1, 129.8, 130.9, 133.6, 136.3, 140.5, 142.4, 143.6, 153.2, 159.8, 189.0.

Compound (XXVI): 3-Methoxybenzyl/Combretastatin Prodrug (DMU-336)

The procedure followed that described for compound (XXV), but using combretastatin (95 mg, 0.3 mmol) in place of the calchone, to give the title 3-methoxybenzyl/combretastatin prodrug. IR (cm$^{-1}$; KBr): (1750) (CO) (1500; ArC=C); Mass Spectrum (M+1) m/e: 437.

Compound (XXVII): 3-Methoxybenzyl/Resorufin Fluorophore Conjugate (DMU-320)

To a solution of triphosgene (139 mg; 46.9 mmol) in dichloromethane (1 ml) was added dropwise a solution of 3-methoxybenzyl alcohol (65 mg; 46.9 mmol) and diisopropylethylamine (0.18 ml; 1.03 mmol) in anhydrous dichloromethane (1 ml). After 20 min of stirring at room temperature a suspension of resorufin (110 mg; 46.9 mmol) and diisopropylethylamine (0.18 ml; 1.03 mmol) in anhydrous dichloromethane/1,3-dimethyl-2-imidazolidinone (1:1; 1 ml) was added dropwise and the mixture was stirred for 18 h. The reaction was quenched with water (10 ml) and a brown precipitate was isolated; the residual/aqueous layer was extracted with ether (3×10 ml). The combined organic layers were washed with brine (3×10 ml), dried over magnesium sulfate and concentrated in vacuo. The precipitate and the residue isolated were combined and purified using preparative thin layer chromatography to afford an orange solid (40 mg; 21%). IR (cm$^{-1}$; KBr): (1750; CO) (1250; OCH$_3$); $^1$H-NMR CDCl$_3$: (3.8, s; 3H) (5.3, s; 2H) (6.4, s; 1H) (6.8, m; 4H) (7.2, m; 4H) (7.8, m; 1H); $^{13}$C-NMR CDCl$_3$: 55.4, 70.9, 107.4, 109.1, 114.1, 114.6, 118.5, 120.8, 129.9, 131.3, 134.8, 135.3, 135.7, 144.4, 153.6, 157.8, 186.3; Mass Spectrum (M+1) m/e: 379.

Compound (XXVIII): 3-Methoxybenzyl/7-Amino-4-methylcoumarin Conjugate (DMU-319)

To a solution of triphosgene (423 mg; 1.42 mmol) in dichloromethane (1 ml) was added dropwise a solution of 3-methoxybenzyl alcohol (177 mg; 1.42 mmol) and diisopropylethylamine (0.545 ml; 3.12 mmol) in anhydrous dichloromethane (1 ml). After 20 min of stirring at room temperature a solution of 7-amino-4-methylcoumarin (250 mg, 1.42 mmol) and diisopropylethylamine (0.545 ml; 3.12 mmol) in anhydrous DMF was added dropwise and the mixture was stirred for 18 h. The reaction mixture was diluted with water (10 ml) and ether (10 ml) and a white precipitate was isolated. The crude precipitate was chromatographed using preparative thin layer chromatography to afford the product as a white solid (50 mg; 10%). IR (cm$^{-1}$; KBr): (1520; ArCH) (1210; OCH$_3$); $^1$H-NMR CDCl$_3$: (2.4, s; 3H) (3.8, s; 3H) (5.2, s; 2H) (6.2, s; 1H) (6.8, m; 3H) (7.1, s; 1H) (7.3, m; 4H); $^{13}$C-NMR CDCl$_3$: 18.6, 29.7, 55.3, 67.3, 105.9, 113.9, 14.0, 14.4, 15.6, 120.5, 125.4, 129.8, 141.4, 152.3, 154.5, 159.9, 161.2; Mass Spectrum (M+1) m/e: 355.

Section 5: Cinnamyl Based Prodrugs

3-Methoxycinnamyl Alcohol

Lithium aluminium hydride (213 mg; 5.5 mmol) was added portionwise to anhydrous THF (10 ml) at 0° C. To this a solution of 3-methoxycinnamic acid (2 g; 11 mmol) in THF (5 ml) was added. The reaction was left to stir at 0° C. for 10 min and then allowed to reach ambient temperature. The reaction mixture was quenched with 2M aqueous sodium hydroxide (15 ml) and the aqueous layer was extracted with ether (3×15 ml). The combined organic layers were washed with 2M hydrochloric acid (3×15 ml), brine (3×15 ml), dried over magnesium sulfate and concentrated in vacuo. The residue was chromatographed on silica gel, and the product was isolated as an oil (222 mg: 12%). IR (cm$^{-1}$; KBr): (3400, OH) (1400; C=C) (1250; OCH$_3$); $^1$H-NMR CDCl$_3$: (3.8, s; 3H) (4.3, dd; 2H) (6.3, m; 1H) (6.6, d; 1H) (6.8, dd; 1H) (6.9, t; 1H) (7.0, d; 1H) (7.2, t: 1H); $^{13}$C-NMR CDCl$_3$: 55.3, 63.6, 111.9, 113.4, 119.2, 128.9, 129.6, 131.0, 138.2, 158.2, 159.9; Mass Spectrum (M$^+$) m/e: 164.

Compound (XXX): 3-Methoxycinnamyl/Mustard Prodrug (DMU-323)

The procedure followed that described for compound (XVIII), but using 3-methoxycinnamyl alcohol (222 mg, 1.35 mmol) in place of 3-methoxybenzyl alcohol. This gave the title 3-methoxycinnamyl/mustard prodrug as an oil (115 mg; 26%). IR (cm$^{-1}$; KBr): (1700; CO) (1500; ArC=C). $^1$H-NMR CDCl$_3$: (3.6, s; 8H) (3.8, s; 3H) (4.7, dd; 2H) (6.3, m; 1H) (6.6, d; 1H) (6.8, dd; 1H) (6.9, q; 2H) (7.2, m; 1H); $^{13}$C-NMR CDCl$_3$: 41.9, 50.6, 51.2, 55.2, 66.3, 111.9, 114.2, 119.3, 123.7, 129.6, 133.9, 137.6, 155.6, 159.8; Mass Spectrum (M$^+$) m/e: 331.

Compound (XXXI): Cinnamyl/Resorufin Fluorophore Conjugate (DMU-325)

The procedure followed that described for compound (XXVII), but using cinnamyl alcohol (250 mg; 1.86 mmol) in place of 3-methoxycinnamyl alcohol to afford the title cinnamyl/resorufin conjugate as an orange solid (40 mg; 6%). $^1$H-NMR CDCl$_3$: (4.9, dd; 2H) (6.3, m; 2H) (6.9, dd; 1H)(7.2, m; 9H) (7.8, m; 1H); $^{13}$C-NMR CDCl$_3$: 63.7, 69.9, 107.3, 109.2, 118.6, 121.3, 127.7, 128.8, 131.3, 134.8, 135.3, 136.3, 144.4, 148.5, 149.3, 152.5, 153.6, 186.3.

Compound (XXXII): Cinnamyl/7-Amino-4-methylcoumarin Fluorophore Conjugate (DMU-324)

The procedure followed that described for compound (XXVIII), but using cinnamyl alcohol (76 mg; 2.5 mmol) in place of 3-methoxybenzyl alcohol to afford the title compound as an oil (3 mg; 2%). ¹H-NMR CDCl₃: (2.4, s; 3H) (4.9, s; 2H) (6.1, s; 1H) (6.2, m; 1H) (6.9, m; 1H) (7.2, m; 8H).

Table 1: Growth Inhibition of Cells not Expressing and Expressing CYP1B1 (IC50/uM±2%)

TABLE 1

| Growth Inhibition of Cells not Expressing and Expressing CYP1B1 (IC50/uM ± 2%) | | | |
|---|---|---|---|
| Compound No. | DMU No. | V79 Cells | V791B1 Cells | Selectivity Factor |
| XVII | DMU-313 | 16.0 | 5.0 | 3.2 |
| XIX | DMU-315 | 3.1 | 1.0 | 3.1 |

What is claimed is:

1. A CYP1B1 substrate comprising a chemical moiety bound to a carrier framework having the formula (Z):

wherein:

X=OH, OMe or N(CH₃)₂; and
n=0–3;

and;

$R_1$=H, $C_{1-4}$ lower alkyl, or together with $R_2$ forms part of a cycloalkyl group which may be further substituted to form part of a polycyclic cycloalkyl group;

$R_2$=H, OMe, $C_{1-4}$ lower alkyl, or together with $R_1$ and/or $R_3$ forms part of a cycloalkyl, polycyclic cycloalkyl, or forms part of a polycyclic aromatic group by linkage to $R_4$;

$R_3$=H, OMe, $C_{1-4}$ lower alkyl or together with $R_2$ forms part of a cycloalkyl, polycyclic cycloalkyl; and

$R_4$=H or is fused directly to the aromatic position designated by $R_2$;

either:
the chemical moiety is derived from a chemical having a free amino, hydroxyl or thiol group and which links it to the rest of the CYP1B1 substrate, such that A represents NH, NR (R=$C_{1-4}$ lower alkyl), C or S; or
the chemical moiety is derived from a chemical having a carboxylate group, an ester linkage joining it to the rest of the CYP1B1 substrate and A being nothing; and
the chemical moiety is selected from the group consisting of a calchone moiety, a colchicine moiety, a stilbene moiety, a daunomycin moiety, an esperimycin moiety, a nitrogen mustard moiety, a staurosporin moiety, a taxol moiety, and a fluorophore moiety.

2. A CYP1B1 substrate according to claim 1 wherein n=2 and $R_2$ and $R_4$ are fused forming a naphthyl group.

3. A CYP1B1 substrate according to claim 1, having a formula selected from the group consisting of:

(XV):

and (XVI):

4. A CYP1B1 substrate according to claim 1, wherein the carrier framework is a substituted benzyl carrier framework.

5. A CYP1B1 substrate according to claim 4, having the general formula (Y):

wherein $R_2$, R3 and X are selected from any one of the groups of:

a) $R_2$=H, $R_3$=H, X=OMe;
b) $R_2$=H, $R_3$=OMe, X=OMe; and
c) $R_2$=OMe, R3=H, X=OMe.

6. A CYP1B1 substrate according to claim 4, having a formula selected from the group consisting of:

(XXIII):

(XXV):

(XXVI):

(XXVII):

(XXVIII):

7. A CYP1B1 substrate according to claim 1, wherein the carrier framework is a cinnamyl carrier framework.

8. A CYP1B1 substrate according to claim 7, having a formula of:

(XXX):

9. A CYP1B1 substrate according to claim 7, having a formula selected from the group consisting of:

(XXXI):

(XXXII):

10. A CYP1B1 substrate comprising a carrier framework having the formula (Z'):

wherein:

X=OH, OMe or N $(CH_3)_2$; and n=0–3;

and;

$R_1$=H, $C_{1-4}$ lower alkyl, or together with $R_2$ forms part of a cycloalkyl group which may be further substituted to form part of a polycyclic cycloalkyl group;

$R_2$=H, OMe, $C_{1-4}$ lower alkyl, or together with $R_1$ and/or $R_3$ forms part of a cycloalkyl, polycyclic cycloalkyl, or forms part of a polycyclic aromatic group by linkage to $R_4$;

$R_3$=H, OMe, $C_{1-4}$ lower alkyl or together with $R_2$ forms part of a cycloalkyl, polycyclic cycloalkyl; and $R_4$=H or is fused directly to the aromatic position designated by $R_2$; and A represents H, NH2, NHR (R=$C_{1-4}$ lower alkyl), OH or SH.

11. A composition comprising a CYP1B1 substrate according to claim 1 and a carrier.

12. A method of inhibiting tumor cell growth comprising:
contacting a tumor cell with a CYP1B1 substrate according to claim 1,
wherein the tumor cell comprises an enzyme having aromatic hydroxylase activity, and the tumor cell is selected from the group consisting of a bladder tumor cell, a brain tumor cell, breast tumor cell, a cervical tumor cell, a colon tumor cell, a connective tissue tumor cell, an endometrium tumor cell, an esophageal tumor cell, a kidney tumor cell, a lung tumor cell, a lymph node tumor cell, an ovarian tumor cell, a prostate tumor cell, a skin tumor cell, an intestinal tumor cell, a stomach tumor cell, a testis tumor cell, and a uterine tumor cell.

13. A method of manufacture of a medicament for the treatment of a tumor, comprising an enzyme having aromatic hydroxylase activity comprising:
providing a CYP1B1 substrate according to claim 1 and combining the CYP1B1 substrate with a carrier,
wherein the tumor is selected from the group consisting of a bladder tumor, a brain tumor, a breast tumor, a cervical tumor, a colon tumor, a connective tissue tumor, an endometrium tumor, an esophageal tumor, a kidney tumor, a lung tumor, a lymph node tumor, an ovarian tumor, a prostate tumor, a skin tumor, an intestinal tumor, a stomach tumor, a testis tumor, and a uterine tumor.

* * * * *